United States Patent [19]

Kamishita et al.

[11] 4,008,321
[45] Feb. 15, 1977

[54] COMPOSITION FOR A TOPICAL PREPARATION AND A PROCESS FOR PRODUCING THE SAME

[75] Inventors: Takuzo Kamishita; Shigeyoshi Hiraki, both of Toyama, Japan

[73] Assignee: Toko Yakuhin Kogyo Kabushiki Kaisha, Osaka, Japan

[22] Filed: Dec. 8, 1975

[21] Appl. No.: 638,916

[30] Foreign Application Priority Data

Dec. 20, 1974 Japan .............................. 49-147110

[52] U.S. Cl. .............................................. 424/243
[51] Int. Cl.² ...................................... A61K 31/56
[58] Field of Search ................................... 424/243

[56] References Cited
UNITED STATES PATENTS

| | | | |
|---|---|---|---|
| 3,749,773 | 7/1973 | Ninger et al. | 424/81 |
| 3,899,580 | 8/1975 | O'Neill et al. | 424/243 |
| 3,924,004 | 12/1975 | Chang | 424/243 |

*Primary Examiner*—Elbert L. Roberts
*Attorney, Agent, or Firm*—Armstrong, Nikaido & Wegner

[57] ABSTRACT

A composition for a topical preparation which comprises a steroid, crotamiton, propylene glycol and a carboxyvinyl polymer in an aqueous medium, said composition having been neutralized with an organic amine, and a process for producing the same which comprises adding a mixed solution of crotamiton and propylene glycol containing a steroid to an aqueous solution of a carboxyvinyl polymer, followed by neutralizing the resultant solution with an organic amine while stirring, to give a transparent, gelatinous topical composition.

10 Claims, 7 Drawing Figures

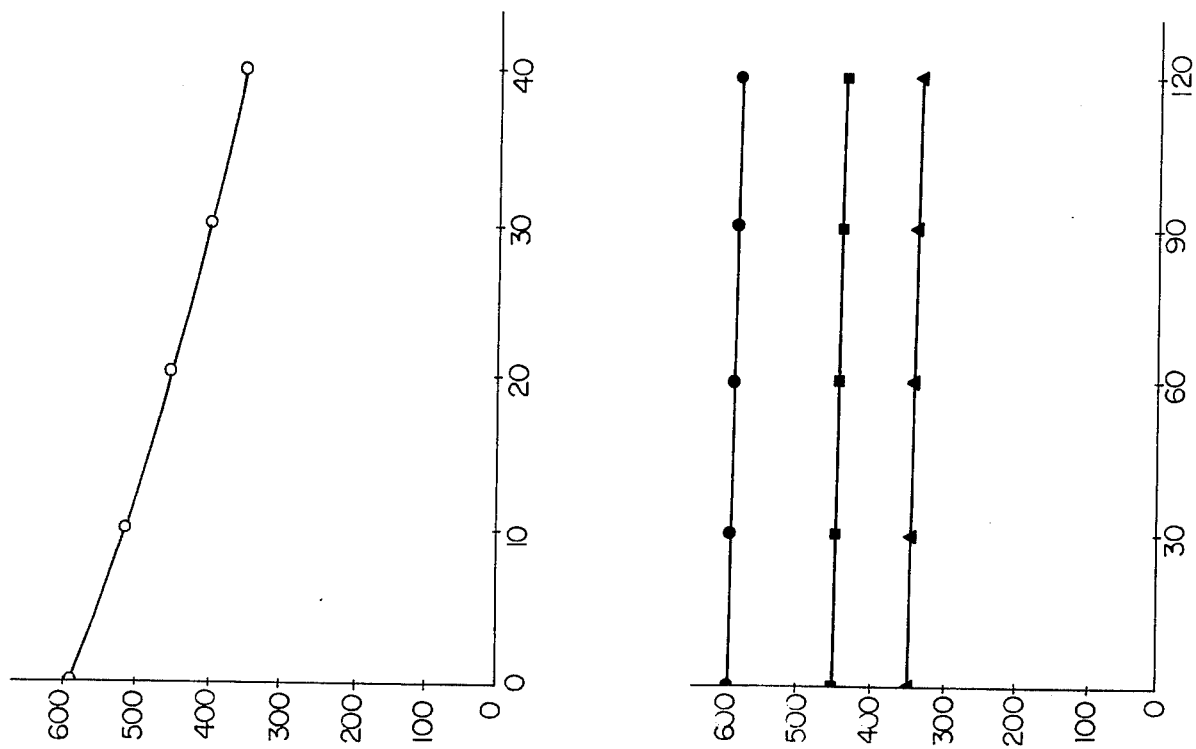
FIG. 2
FIG. 3
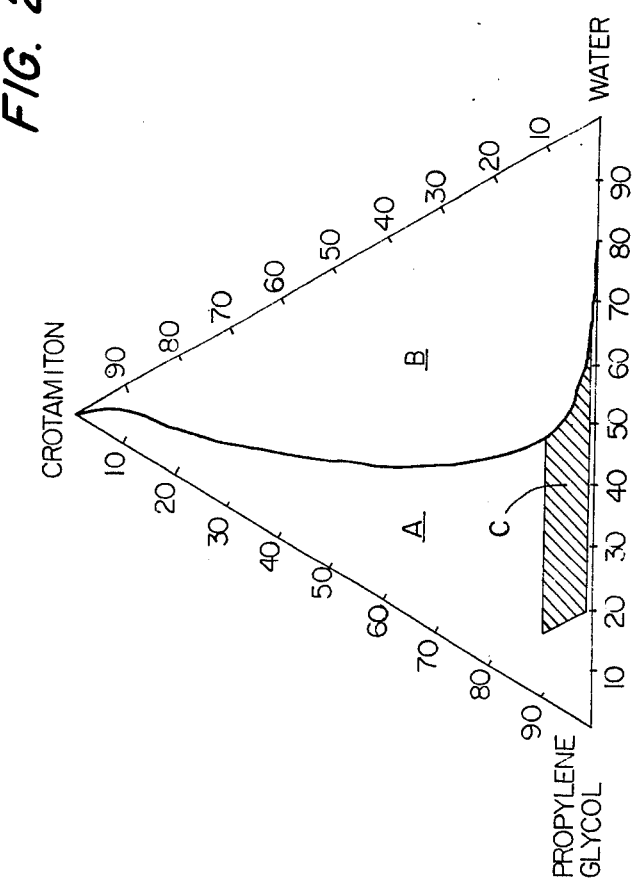
FIG. 1

COMPOSITION FOR A TOPICAL PREPARATION AND A PROCESS FOR PRODUCING THE SAME

BACKGROUND OF THE INVENTION

Steroids, adrenal cortical hormones, such as, prednisolone, dexamethasone and cortisone, have been used in the forms of ointments or liquors for anti-imflammatory topical preparations, since the steroids have excellent anti-imflammatory activity.

However, when such an ointment is applied to the skin, it produces an unpleasant stickiness on the skin and soils clothing which might be worn over the ointment. Furthermore, absorption of the active ingredients (steroids) through the skin is not sufficient, and the ointment is separated from the skin by the rubbing action of the clothing. When liquor is applied to the skin, the liquor is run down from the applied skin.

In order to obtain the pharmaceutical effects from steroids and to obtain a preparation which does not have on unpleasant stickiness on the skin, the preparation should satisfy, for example, following points:

1. The steroid should be dissolved in the preparation in order to provide sufficient pharmaceutical effects. When crystals and/or powders of the steroid are included in the preparation, the steroid may not be absorbed from the skin sufficiently, and therefore, the pharmaceutical effects are not fully utilized. When the steroid is dissolved in the preparation, the steroid is satisfactorily absorbed into the skin and sufficient pharmaceutical effects are obtained.
2. The steroid should be released from the preparation when applied to the skin. In other words, the steroid should be easily separable from the base preparation, contact the skin and be supplied to the skin in a manner such that complate absorbption is possible.
3. The preparation should be stable to changes in temperature and during prolonged storage. It is desirous that the preparation maintains the same properties during both summer and winter seasons, and does not change in quality during prolonged storage. Furthermore, the preparation should be adhesive and extensive to the skin, in proper degree.
4. Unpleasant properties, such as stickiness and stimulus of the preparation. Should be avoided after application to the skin.

When an ointment is applied to the skin, it produces unpleasant stickiness on the skin for a long period. Furthermore, the steroid is not always dissolved sufficiently in the preparation. Even though the steroid may be dissolved in the preparation, absorption of steroid through the skin is not sufficient, because the steroid is included in or retained by the oils and/or surface active agents which are used as bases for the ointment. The absorption of the steroid included in the preparation is also not expected, because the applied preparation is often removed from the skin by the rubbing action of clothing. In general, ointments are not stable for changes in temperature, such as different temperatures between summer and winter seasons. For example, there is a tendency for ointments to become soft or liquid during the summer season and to become hard or solid in winter. Therefore, ointments are inconvenient for practical use.

In preparations such as liquors, it is also not expected that the active ingredient would be absorbed, because the adhesion of the liquor to the skin is inferior and the liquor runs and is lost from the area of the skin to which it has been applied.

We have carried out investigations in order to improve the above mentioned defects and to obtain a favourable preparation satisfying the above points for topical use.

It is known that polymer compounds, such as methyl cellulose and carboxymethyl cellulose, form membranes on the skin after application thereof. It is necessary, however, to use large quantities of such polymers to make a gelationous preparation containing steroids as the active ingredient, in order to obtain topical preparation having the appropriate viscosity. We have also observed that such preparations are sticky when applied to the skin, because considerable time is necessary for the formation of the membranes.

We have now found that by using a very small quantity of a carboxyvinyl polymer, excellent topical preparations are obtained, which are not sticky when applied to the skin and membranes are formed quickly. Furthermore, the active ingredient (steroid) is sufficiently absorbed through the skin without loss and provides the desirable results.

We have also found that the colloidal state of the preparations, when applied to the skin, is broken down by a small amount of salts, such as sodium chloride, present in perspiration, as a result of which the absorption of the active ingredients (steroids) is increased.

SUMMARY OF THE INVENTION

This invention relates to a composition for a topical preparation which comprises a steroid, crotamiton, propylene glycol and a carboxyvinyl polymer in an aqueous medium, said composition having been neutralized with an organic amine, and containing crotamiton in an amount of from 0.5 to 10% by weight, propylene glycol in an amount of from 20 to 80% by weight, water in an amount of from 10 to 80% by weight and carboxyvinyl polymer in an amount of from 0.3 to 1.5% by weight of the composition, and a process for producing the same which comprises adding a mixed solution of crotamiton and propylene glycol containing a steroid to an aqueous solution containing carboxyvinyl polymer, followed by neutralizing the resulting solution with an organic amine to provide a transparent, gelatinous, topical composition.

BRIEF DESCRIPTION OF THE DRAWINGS

FIG. 1 is a graph having triangular coordinates showing the ratio of three ingredients, crotamiton, propylene glycol and water, at 20° C.

FIGS. 2 to 7 are graphs showing the change of viscosity of the preparation under various temperatures and under storage for long periods.

FIGS. 2, 4 and 6 are the graphs showing viscosities of the preparation described in Examples 1, 2 and 3, respectively. In the graphs, the horizontal lines show temperature (° C) and the vertical lines show viscosity (poise).

FIGS. 3, 5 and 7 are the graphs showing the viscosities of the preparations described in Examples 1, 2 and 3, respectively which have been stored for long periods. In the graphs, the horizontal lines show time (days) and the vertical lines show viscosity (poise).

In the FIG. 1, A represents the range in which the three ingredients are dissolved homogeneously, B represents the range in which white turbidity appears, and C is the range in which the preferred preparations are obtained within the scope of A.

Figure 5:
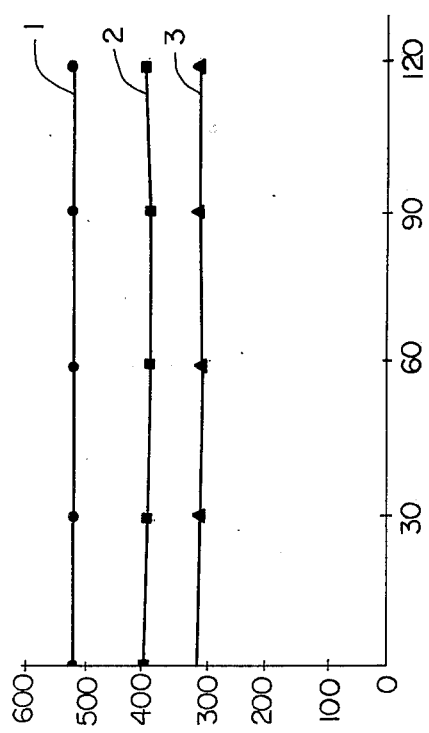
Figure 7:
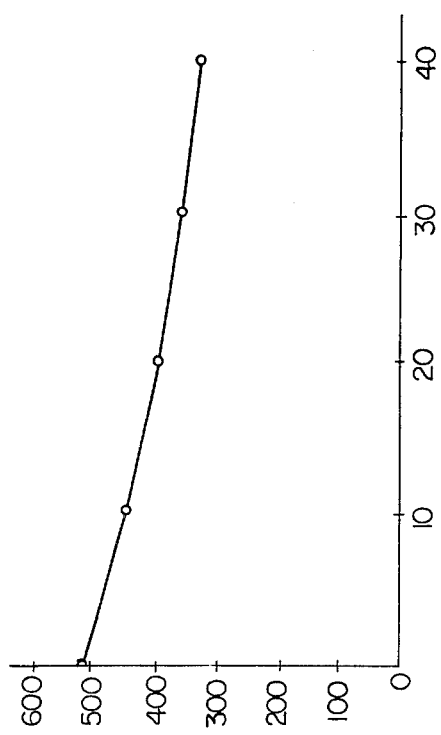

In the FIGS. 3, 5 and 7, line 1 represents the viscosity for the preparation stored at 0° C, line 2 at 20° C and line 3 at 40° C, respectively.

DETAILED DESCRIPTION OF THE INVENTION

According to the present invention, there is provided a transparent, gelatinous composition for a topical preparation which comprises a steroid, crotamiton, propylene glycol and a carboxyvinyl polymer in an aqueous medium, said composition having been neutralized with an organic amine, and containing crotamiton in an amount of from 0.5 to 10% by weight, propylene glycol in an amount of from 20 to 80% by weight, water in an amount of from 10 to 80% weight and a carboxyvinyl polymer in an amount of from 0.3 to 1.5% by weight of the composition. The present invention also provides a process for the production of the composition which comprises adding a transparent mixed solution of crotamiton and propylene glycol containing a steroid to an aqueous solution containing carboxyvinyl polymer, followed by neutralizing the resulting solution with an organic amine while stirring, to provide a transparent gelatinous topical composition.

In general, steroids are insoluble in water, however, are very soluble in crotamiton, (such as, N-crotonoyl-N-ethyl-o-toluidine). Crotamiton is insoluble in water and is separated from water. We have found that colorless, transparent homogeneous solutions are obtained when a specified amount of propylene glycol is added to a mixture containing crotamiton and water. Propylene glycol is useful not only to obtain a colorless, transparent composition, but also to stabilize the gelatinous state of the composition.

In general, steroids are slightly soluble in propylene glycol, and therefore it is impossible to obtain a preparation containing steroids in high concentration. Moreover, these is a tendency of steroids to form crystals when stored at lower temperatures. As a result, it is not preferable to use propylene glycol alone. Moreover, steroids crystallize more easily in a mixture of propylene glycol and water. However, water is necessary to obtain a gelatinous composition. Therefore, crotamiton is very effective to obtain a gelatinous compositions in accordance with the present invention which contain steroids in high concentrations.

The steroids that may be employed in accordance with the present invention include prednisolone, dexamethasone, triamcinolone, β-methasone, cortisone and esters thereof, other adrenal cortical hormones and the like.

The carboxyvinyl polymers that may be employed in accordance with the present invention are vinyl polymers with active carboxyl groups, white powder, highly ionic and slightly acidic, and hydrophylic polymers which can be prepared by polymerising a monomer mixture consisting mainly of acrylic acid, as shown in Chem. Eng. News 36, No. 39, P 64 (Sept. 29, 1958). Carbopol 934, 940 and 941, which are available commerically from the Goodrich Chemical Co., can also be used in the present invention.

The ratio of three ingredients, crotamiton, propylene glycol and water, are shown in the graph of triangular coordinates in FIG. 1 of the accompanying drawings. FIG. 1 shows the ratio of the three ingredients at 20° C. In FIG. 1, A represents the range within which the three ingredients are dissolved homogeneously. B represents the range within which white turbidity appears. C represents the range within which desirable or preferred compositions are obtained within the range of A.

Crotamiton is used in order to dissolve steroid. If crotamiton is used in an amount of less than 0.5% by weight of the preparation, it is not advisable, since the active ingredient (steroid) is not dissolved sufficiently. It is not necessary to use crotamiton, in order to dissolve steroid, in an amount of more than 10% by weight of the composition, because steroids are, generally, used in an amount of less than 1% by weight of the composition. The amount of steroid to be used is varied with the kind of steroids employed, that is, the steroids should be contained in the composition in an amount such that the desired pharmaceutical effects are observed. For that reason, steroids are generally used in an amount of from about 0.001 to about 1% by weight of the composition. When propylene glycol is used in a large amount, the preparation obtained is sticky and the formation of membranes and drying time on the skin are delayed, although the composition is transparent. When propylene glycol is used in small amounts, the object of the present invention can not be realized, since the preparation becomes turbid, because the water and crotamiton are not mixed homogeneously. Therefore, use of propylene glycol in an amount from 20% by weight to 80% by weight of the composition is preferable in the present invention. On the other hand, when water is used in a small amount, the composition obtained is sticky, and when water is used in a large amount, it is difficult to obtain a transparent solution. Use of water in an amount from 10% by weight to 80% by weight of the composition is preferable in the present invention. As is clear from FIG. 1, however, there are situations where a monogeneous solution can not be obtained, even if propylene glycol is used in more than 20% by weight and/or water is used in less than 80% by weight of the composition, when a large amount of crotamiton is used.

It is possible to obtain transparent and homogeneous solution using a small amount of water and a large amount of propylene glycol, if a large amount (around 10% by weight) of crotamiton is used and, using a large amount of water and a small amount of propylene glycol, if a small amount (around 0.5% by weight) of crotamiton is used.

Carboxyvinyl polymers are included in the composition in an amount of from 0.3 to 1.5% by weight. The carboxyvinyl polymer is effective in obtaining a suitable viscosity for the composition by gelatin and to form a membrane when applied to the skin. When carboxyvinyl polymers are used in amounts less than 0.3% weight, the desirable effects are not observed. On the other hand, when carboxyvinyl polymer is used in amounts more than 1.5% by weight, the composition obtained is too viscous, and the formation of the membrane on the skin and breakdown of gel state by salt on the skin are delayed, and these results are not desirable.

The carboxyvinyl polymers have free carboxy groups in the molecule and thus provides an acidic solution when dissolved in water. Organic amines are used to neutralize the acidity of the carboxyvinyl polymer solution. Such amines include triethanolamine, diethylamine, diisopropanolamine and the like, and also include other alkylamines and alkanolamines. The organic amines are used in an amount such that the pH of the composition is slightly acidic or neutral. The pH of the compsotion is arranged in the range of from 5.0 to 7.5, and preferably from 5.5 to 6.5. When the pH of the composition is higher than the above limit, there is a tendency to decompose the steroids, and when the pH of the composition is lower than the above limit, there is a tendency to cause irritation to the skin.

The topical preparation of the present invention can be produced by dissolving a steroid in crotamiton and adding propylene glycol to the resulting solution while stirring, to provide a homogeneous solution, then adding an aqueous solution of a carboxyvinyl polymer to the solution, again while stirring, and finally adding an organic amine, while stirring, to provide a homogeneous solution.

The composition obtained is colorless, gelationous and transparent, and its pH value is slightly acidic or neutral. The preparation is very stable, even at higher temperatures, such as 40° C, and at lower temperatures, such as 0° C, and its viscosity remains almost unchanged even after prolonged storage.

When the composition is applied to the surface of the skin, the gelatinous state is broken down by salts, such as sodium chloride and the like, secreted from the surface of the skin, to form a liquid. As a result, absorption of the active ingredient (steroid) is increased. The carboxyvinyl polymer membrane which is formed is dried by air, and has good durability, and the composition, applied to the skin as a thin membrane, does not stick to clothing. As a result, the composition of the present invention is very durable and the active ingredient has a much longer period of activity than presently known preparations.

The following examples are provided for the purpose of illustrating the present invention and are not intended to limit the scope thereof. In the examples, "JP" means the Japanese Pharmacopoeia and "purified water" means water purified by ion-exchange resins.

EXAMPLE 1

| Composition: | | |
|---|---|---|
| prednisolone | (J P) | 5.00 g |
| crotamiton | | 30.00 g |
| propylene glycol | (J P) | 450.00 g |
| purified water | (J P) | 503.25 g |
| Carbopol 940 | | 5.00 g |
| triethanolamine | (J P) | 6.75 g |

5.00 g of prednisolone were dissolved in 30.00 g of crotamiton, and 450.00 g of propylene glycol were added to the above solution, while stirring, to give a homogeneous solution.

The obtained solution was added to an aqueous solution containing 5.00 g of Carbopol 940 dissolved in 503.25 g of purified water, while stirring, to give a homogeneous solution. Finally, 6.75 g of triethanolamine were added to the solution, again with stirring, to give 1,000.00 g of the composition. The composition obtained was a colorless and transpasent gel having the pH value of 6.5.

The mutual relation of temperature and viscosity of this composition is shown in FIG. 2, that is, the viscosity changes only slightly when exposed to changes in temperature. Therefore, this composition may be used both in summer and winter. The viscosity of this composition remained almost unchanged even after prolonged storage at higher temperatures, 40° C, and at lower temperature, 0° C, for 4 months, as shown in FIG. 3. As a result, it was found that this composition was very stable.

COMPARATIVE EXAMPLE 1

| Composition: | | |
|---|---|---|
| prednisolone | (J P) | 5.00 g |
| crotamiton | | 50.00 g |
| propylene glycol | (J P) | 300.00 g |
| purified water | (J P) | 633.25 g |
| Carbopol 940 | | 5.00 g |
| triethanolamine | (J P) | 6.75 g |

In the manner as described in Example 1, a composition was prepared using above mentioned ingredients. However, the composition was turbid and not transparent. This is due to the fact that this composition falls into the range B of FIG. 1. To obtain a transparent gelatinous solution containing crotamiton in an amount of 5% by weight, propylene glycol should be used in an amount of more than 45% by weight and purified water in an amount less than 55% by weight of the composition.

COMPARATIVE EXAMPLE 2

| Composition: | | |
|---|---|---|
| prednisolone | (J P) | 5.00 g |
| crotamiton | | 50.00 g |
| propylene glycol | (J P) | 833.25 g |
| purified water | (J P) | 100.00 g |
| carbopol 940 | | 5.00 g |
| triethanolamine | (J P) | 6.75 g |

In the manner described in Example 1, a colorless, transparent and gelatinous solution was prepared. This composition, however, was sticky and unpleasant when applied to the skin, and breakdown of the gelatinous state by salts was delayed, moreover, dryness and formation of the membrane was also delayed. This composition falls into the range of B, but does not fall into the scope of C in FIG. 1.

EXAMPLE 2

| Composition: | | |
|---|---|---|
| dexamethazone | (J P) | 1.00 g |
| crotamiton | | 10.00 g |
| propylene glycol | (J P) | 360.00 g |
| purified water | (J P) | 619.60 g |
| Carbopol 940 | | 4.00 g |
| triethanolamine | (J P) | 5.40 g |

1.00 g of dexamethazone was dissolved in 10.00 g of crotamiton, and this solution was added to 360.00 g of propylene glycol, while stirring, to give a homogeneous solution. The solution obtained was added to an aqueous solution containing 4.00 g of Carbopol 940 dissolved in 619.60 g of purified water. Finally, 5.40 g of triethanolamine were added to the solution, with stirring, to give 1000.00 g of homogeneous composition. The composition obtained was colorless and transparent gel having the pH value of 6.5.

Figure 4:
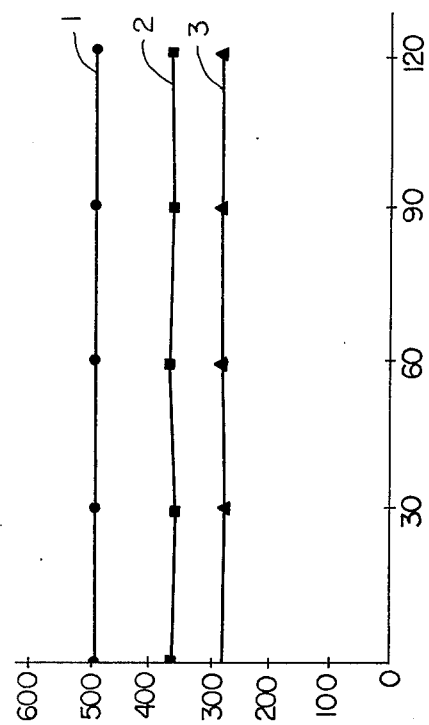

The mutual relation of temperature and viscosity of this composition is shown in FIG. 4. The change on prolonged storage is shown in FIG. 5. In both of the Figures substantially the same results as those of Example 1 were observed. It was found that this composition was very stable.

EXAMPLE 3

| Composition: | | |
|---|---|---|
| triamcinolone | (J P) | 1.00 g |
| crotamiton | | 50.00 g |
| propylene glycol | (J P) | 500.00 g |
| purified water | (J P) | 437.25 g |
| Carbopol 940 | | 5.00 g |
| triethanolamine | (J P) | 6.75 g |

1.00 g of triamcinolone was dissolved in 50.00 g of crotamiton and this solution was added to 500.00 g of propylene glycol, while stirring, to give a homogeneous solution. The solution obtained was added to an aqueous solution of 5.00 g of Carbopol 940 dissolved in 437.25 g of purified water. Finally, 6.75 g of triethanolamine were added to the solution, with stirring to give 1000.00 g of homogeneous composition. The composition obtained was a colorless, transparent, colloidal solution having the pH value of 6.5.

Figure 6:
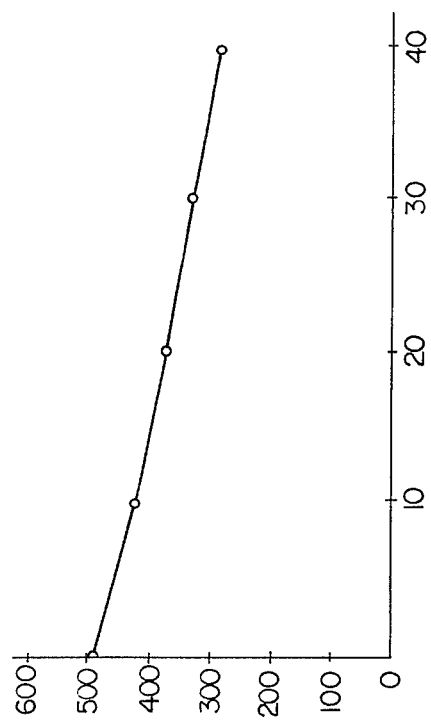

The mutual relation of temperature and viscosity of this composition is shown in FIG. 6, and changes on prolonged storage are shown in FIG. 7. In both Figures, substantially the same results as those of Example 1 were observed. It was found that this composition was very stable.

What is claimed is:

1. A transparent, gelatinous topical composition which comprises a steroid selected from the group consisting of prednisolone, dexamethasone, triamcinolone, β-methasone and cortisone; crotamiton, propylene glycol and a carboxyvinyl polymer in an aqueous medium, said composition having been neutralized with an organic amine selected from the group consisting of alkylamines and alkanolamines, and containing crotamiton in an amount of from 0.5 to 10% by weight, propylene glycol in an amount of from 20 to 80% by weight, water in an amount of from 10 to 80% by weight and carboxyvinyl polymer in an amount of from 0.3 to 1.5% by weight of the composition.

2. The composition according to claim 1, wherein the steroid is present in an amount of from about 0.001 to about 1% by weight of the composition.

3. The composition according to claim 1, wherein the alkylamines and alkanolamines are selected from the group consisting of triethanolamine, triethylamine, diethylamine and diisopropanolamine.

4. A process for preparing a topical composition which comprises preparing a transparent mixed solution containing crotamiton, propylene glycol and a steroid selected from the group consisting of prednisolone, dexamethasone, triamcinolone, β-methasone and cortisone, adding the solution to an aqueous solution containing carboxyvinyl polymer and neutralizing the resulting solution with an organic amine selected from the group consisting of alkylamines and alkanolamines to provide a transparent, gelatinous topical preparation.

5. The process according to claim 4, wherein crotamiton is used in an amount of from 0.5 to 10% by weight of the composition.

6. The process according to claim 4, wherein propylene glycol is used in an amount of from 20 to 80% by weight of the composition.

7. The process according to claim 4, wherein water is used in an amount of from 10 to 80% by weight of the composition.

8. The process according to claim 4, wherein carboxyvinyl polymer is used in an amount of from 0.3 to 1.5% by weight of the composition.

9. The process according to claim 4, wherein the steroid is used in an amount of from about 0.001 to about 1% by weight of the composition.

10. The process according to claim 4, wherein the alkylamines and alkanolamines are selected from the group consisting of triethanolamine, triethylamine, diethylamine and diisopropanolamine.

* * * * *